United States Patent [19]

Lehmann et al.

[11] Patent Number: 4,520,172

[45] Date of Patent: May 28, 1985

[54] METHOD FOR COATING MEDICAMENTS

[75] Inventors: Klaus Lehmann, Rossdorf; Dieter Dreher, Darmstadt; Hubert Rauch, Weiterstadt; Werner Siol, Pfungstadt, all of Fed. Rep. of Germany

[73] Assignee: Röhm GmbH, Darmstadt, Fed. Rep. of Germany

[21] Appl. No.: 474,469

[22] Filed: Mar. 11, 1983

[30] Foreign Application Priority Data

Mar. 11, 1982 [DE] Fed. Rep. of Germany ....... 3208791

[51] Int. Cl.³ ........................... C08F 8/28; C08F 8/12; C08F 8/44
[52] U.S. Cl. ................................... 525/369; 524/561; 525/329.7; 526/240; 526/241; 526/317
[58] Field of Search ............................. 525/329.7, 369; 524/561; 526/240, 241, 317; 427/3, 212, 385.5

[56] References Cited

U.S. PATENT DOCUMENTS 4,112,215 9/1978 Boessler et al. ..................... 526/263
4,433,076 2/1984 Bauer et al. ......................... 523/342

FOREIGN PATENT DOCUMENTS 2512238 1/1977 Fed. Rep. of Germany .

Primary Examiner—Joseph L. Schofer
Assistant Examiner—T. M. Reddick
Attorney, Agent, or Firm—Curtis, Morris & Safford

[57] ABSTRACT

What are disclosed are methods for dispersing a powdered salt-forming synthetic resin in water in the presence of an agent forming a salt with said resin, methods for coating pharmaceutical dosage forms with a dispersion made by such a method, and powdered mixtures of a salt forming resin and salt forming agent for dispersion in water.

9 Claims, No Drawings

METHOD FOR COATING MEDICAMENTS

The present invention relates to methods for making an aqueous dispersion of a powdered synthetic resin, to methods for coating pharmaceutical dosage forms with such a dispersion, and to powdered synthetic resin compositions for making such dispersions.

It is known from published German patent application No. 21 35 073 to coat pharmaceutical dosage forms with an aqueous dispersion of a synthetic resin formed from vinyl monomers, which resin comprises from 10 to 55 weight percent of monomers having a carboxyl or amino ester group. Coating with aqueous dispersions of coating materials has the advantage over using organic coating solutions that the risk of fire and the environmental pollution which organic solvents entail are avoided. However, it also has the drawback that preparation of the aqueous coating dispersions is difficult and cannot be handled by the drug manufacturer. The manufacturer, rather, has to procure the binder in the form of a dispersion thereof, i.e. together with the dispersing water, and store them both. In contrast, he can readily prepare organic coating solutions himself from powdered coating materials.

While according to published German patent application No. 25 12 238 (=U.S. Pat. No. 4,112,215) aqueous dispersions of binders for drug coatings can be converted to powder form by spray drying, the powder must then be dissolved in an organic solvent for use.

According to pending German patent application No. P 30 49 179, as yet unpublished, drug coatings are produced from a spray dried emulsion polymer powder by suspending the powder in an aqueous solution of a nonvolatile plasticizer and applying the suspension to dosage forms and heating them, with part of the water then evaporating and the suspended coating powder passing into solution in the plasticizer. The solution then coalesces to form a coating film and solidifies upon cooling. This process is known as thermogelation. Film formation here differs greatly from that occurring with genuine aqueous latices. There the cohesion pressure between the latex particles during the gradual evaporation of the water is decisive, that is to say the latex particles per se form a coherent film directly, not by way of an intermediate stage as a solution.

Thermogelation does not always meet all the requirements which a coating process for pharmaceutical dosage forms (and the coating materials used with it) should meet. Since the coating powder is not redispersed as a latex but is suspended in the form of particles of fairly large size, the suspension often cannot be stored for a sufficiently long period of time. To obtain a smooth and perfectly pore free coating, substantial amounts of plasticizer and high gelation temperatures must be used, since otherwise rough, more or less porous, coatings are formed unless very thick layers are applied.

The present inventors have set themselves the task of combining the advantages of coating pharmaceutical dosage forms with a coating dispersion with those of using dry coating powders. The object was to develop a process that would not require large amounts of plasticizer and high film forming temperatures, but would yield smooth and pore free coatings. Moreover, an aqueous coating material which could be stored for an extended period of time was to be used. These advantages are obtained by a method for making an aqueous dispersion of a synthetic resin binder, said dispersion being adaptable to the coating of pharmaceutical dosage forms which method comprises adding a powdered synthetic resin binder, capable of salt formation, to water and dispersing said resin in the presence of such an amount of a salt forming agent reacting with said resin that, after reaction from 0.1 to 10 percent of said resin, by weight, is present in salt form, said resin being prepared by the free radical emulsion polymerization of (A) from 20 to 85 percent by weight of at least one alkyl acrylate or alkyl methacrylate, (B) from 80 to 15 percent by weight of at least one vinyl or vinylidene monomer capable of salt formation, (C) from 0 to 30 percent by weight of at least one other vinyl or vinylidene monomer copolymerizable with (A) and (B).

In the present specification and claims, the term "binder" refers to the film forming component of the coating material, whether or not it is used in combination with undissolved auxiliary agents. In the absence of additives, film formation thus can result in a clear polymer coating and, in the presence of undissolved additives, in a cover coat. Film formation occurs directly from the latex state. In the powdered emulsion polymer used, the latex particles are present in their original shape but are agglomerated into loose aggregates. They can therefore be dispersed nearly completely into individual latex particles.

The binder to be used in the preparation of an aqueous coating material can be stored in a space saving and weight saving manner and without the risk of loss in quality as a dry powder, until the coating material is prepared. During redispersion, all other additives can be incorporated into the coating material along with the binder. An aqueous coating material that can be stored for extended periods of time is so obtained.

Although conventional plasticizers may also be incorporated in the coating material to secure the desired film hardness and elasticity, they are not needed in amounts that would make the film soft and tacky during its formation. The process in accordance with the invention thus offers a substantial advantage over the production of coatings from organic solutions which are used as such or are formed as an intermediate step by the thermogelation process. In the latter, drying always involves a very sticky phase.

The reduced tackiness, or, usually, the complete absence of tackiness, is due also to the lower film forming temperature. Film formation from latex dispersions occurs considerably below the temperature range in which the coating material becomes tacky. Therefore, that temperature range can readily be avoided.

Depending on whether the salt forming groups in the emulsion polymer of the invention are acidic or basic, coatings resistant to gastric fluid or soluble in intestinal or gastric fluids are obtained. Surprisingly, partly neutralized coatings containing carboxyl groups remain undissolved in an acid or even neutral medium. In a weakly alkaline medium, coatings with a low carboxyl group content will dissolve slowly, whereas with rising carboxyl group content they will dissolve more quickly. Coatings can therefore be formulated to dissolve at a site and time consistent with the pharmacological action of the drug.

The coatings may be applied to pharmaceutical dosage forms as a single layer or as one of several layers. Like known coatings containing organically dissolved binders of the same or of a similar chemical composition, the coatings produced in accordance with the invention may form the ground or cover coats or the intermediate coats of multilayer coatings. Dosage forms which can be coated in accordance with the invention include tablets, dragées, capsules, pellets and granules. The latter can also be molded to give matrix tablets.

The emulsion polymer may be prepared by the process described in published German patent application 21 35 073. Emulsion polymers containing up to about 70 weight percent of monomers having carboxyl groups may be prepared, for example, by the process of published European patent application No. 73 296, according to which a monomer phase principally containing acrylic and methacrylic monomers is added to a water phase in the presence of a free radical initiator and an emulsifier. Part of the emulsifier, for instance from 0.5 to 60 percent by weight thereof, is added to the water phase prior to polymerization: the remaining emulsifier, e.g. 40 to 99.5 percent by weight thereof, is dissolved in the monomer phase.

Alkyl esters of acrylic or methacrylic acid which enter into the composition of the emulsion polymer as monomer component (A) are especially those having from 1 to 8 carbon atoms in the alkyl group. Methyl acrylate and methacrylate and ethyl acrylate and methacrylate are preferred.

The vinyl or vinylidene monomer component (B) capable of salt formation may contain carboxyl groups, in which case it will be capable of forming salts with bases, or it may contain primary, secondary, or tertiary amine groups, in which case it will be capable of forming salts with acids. Suitable acidic monomers are, in particular, acrylic or methacrylic acid and mixtures thereof. Other acidic monomers are maleic, fumaric, and itaconic acid, for example, and half esters or half amides of these acids. Suitable monomers having amino groups and vinyl imidazole, vinyl imidazoline, vinyl imidazolidine, vinyl pyridine, the mono- or di-alkylaminoalkyl esters or mono- or di-alkylaminoalkylamides of unsaturated polymerizable carboxylic acids, such as cyclohexylaminoethyl acrylate and methacrylate, dimethylaminoethyl acrylate and methacrylate, diethylaminoethyl acrylate and methacrylate, morpholinoethyl acrylate and methacrylate, piperidinoethyl acrylate and methacrylate, 4-dimethylaminobutyl acrylate and methacrylate, dimethylaminoneopentyl acrylate and methacrylate, and N-dimethylaminoethyl acrylate and methacrylamide.

In addition, further vinyl or vinylidene comonomers, designated (C), may optionally be part of the composition of the polymer, for example, acrylamide or methacrylamide, hydroxyalkyl esters of acrylic acid or of methacrylic acid, vinyl esters, vinylpyrrolidone, or lower olefins such as ethylene or propylene, or styrene.

The quantitative ratio of the monomer components (A) and (B), and optionally (C), depends on both the requirements of the coating process and on the pharmacological behavior of the coating. The emulsion polymer must be storable in powder form, in the nonglassy state, at room temperature. This requires a glass transition temperature about 25° C., and preferably above 40° C. The glass transition temperature is lowered by the components (A), except for methyl and ethyl methacrylate, and raised by the last mentioned esters and most of the monomers of component (B). A decrease in the glass transition temperature will be coupled with an increase in the elasticity and extensibility of the film. Conversely, the hardness and brittleness of the film will increase with the glass transition temperature.

The amount of the plasticizing monomers, such as acrylic alkyl esters and higher methacrylic alkyl esters, must therefore be high enough to permit film formation at moderate temperatures and to result in a film of adequate elasticity. The hardening monomers with which the glass transition temperature can be raised to the desired level can belong to component (A) and/or (B). Of the monomers making up the component (B), it is particularly acrylic acid and methacrylic acid and their salts which have a hardening effect, while that of the aminoalkylamides is less and that of the aminoalkyl esters still less. Thus, if the necessary hardness cannot be obtained with the monomers (B) alone, methyl methacrylate or ethyl methacrylate should be made a part of component (A).

Coatings which are resistant to gastric juice are obtained when the monomers of component (B) contain carboxyl or carboxylate groups. With high contents of these groups, the coatings will dissolve rapidly in alkaline intestinal fluid, whereas with low contents they will dissolve more slowly or through swelling become permeable to diffusion. Monomers containing amino groups, if present in large percentages, will render the coating soluble in gastric juice, and if present in low percentages will render it capable of swelling in gastric juice and permeable to diffusion.

The emulsion polymer is usually prepared in the presence of anionic, cationic, or nonionic emulsifiers, or compatible mixtures thereof, in the form of an aqueous latex with a solids content ranging from 30 to 70 weight percent, for example. In recovering a solid polymer powder from the latex, care must be taken to assure that the latex particles are preserved as such and do not agglutinate into aggregates which cannot be broken up. This can be done by avoiding temperatures above the minimum film forming temperature in isolating the polymer. Suitable methods are, in particular, spray drying and freeze drying. The latter can be employed even with polymers at the lower limit of the range of suitable glass transition temperatures. The dried emulsion polymer will be present in the form of a fine white powder, but its particles will usually consist, not of individual latex particles, but of loose aggregates of many latex particles which can be reduced without any expenditure of energy. When pressing with a pin on a powder particle causes splintered fragments to break off, this is an indication that the latex particles are glassy and insolubly agglomerated. The preparation of the powdered emulsion polymer is not part of the invention.

The emulsion polymer contains monomeric units having acidic or basic groups in the salt forming component (B). Salt formation by the acid groups occurs through reaction with a base. Suitable bases are alkalis, for example sodium hydroxide, potassium hydroxide, sodium carbonate, potassium carbonate, sodium bicarbonate, trisodium phosphate, trisodium citrate, or ammonia, or physiologically compatible amines such as triethanolamine or tris(hydroxymethyl)aminomethane. Ammonia is particularly effective and is an effective redispersant even in a concentration of 0.1 weight percent, and in particular of 0.5 weight percent, whereas other bases often exhibit adequate effectiveness only in concentrations of 1 weight percent and up.

The monomeric units containing amino groups are converted to the salt form with acids. Physiologically compatible acids are hydrochloric acid, phosphoric acid, citric acid, acetic acid, and tartaric acid, for example.

The conversion of a limited amount of the salt forming units (B) to the salt form is of considerable importance for the redispersion of the emulsion polymer. The controlling factor is not the absolute amount of the salt forming medium but the amount of weight of units (B) which are converted to the salt form. When that amount is less than 0.1 weight percent, based on the total weight of the unneutralized emulsion polymer, adequate redispersion will not be secured. When the amount is above 10 weight percent, the latex particles will swell considerably or dissolve completely. In either case, a satisfactory film can no longer be produced. The amount of the salt forming medium used preferably is not greater than that barely required to secure sufficiently stable redispersion. The best results are usually obtained with an amount from 0.5 to 5 weight percent of monomeric units (B) in salt form. The range from 1.0 to 3 weight percent is particularly preferred.

The conversion of the salt forming groups to the salt form may take place in several steps. For example, the salt forming medium or part thereof may be added to the original aqueous dispersion from which the polymer powder is produced. As a rule, however, the dry polymer powder will contain no salt forming groups. The salt forming medium can then be mixed with the polymer powder, optionally partially, in the form of a powder. Suitable salt forming media in powder form are soda and citric acid, for example. Preferably the salt forming medium is used only during redispersing. The polymer powder is stirred into the aqueous solution of the salt forming medium, for example. Preferably, however, it is added only after the polymer powder has been stirred into water, appropriately in the form of an aqueous solution. The polymer powder then passes into the latex state. This is best accomplished with moderate stirring. If agitation is too vigorous, coagulate may form. The proportion of coagulate or of aggregates which are markedly larger than the original latex particles should not exceed 20 weight percent, based on the polymer powder used. At least 80 weight percent of the polymer should be present in the form of latex particles with diameters ranging from 0.1 to 5 microns. As a rule, the particle size will substantially correspond to that of the original latex or, because of slight swelling, will be somewhat larger. In many cases, it will help in redispersing to add a small amount of a suitable surface active agent, although normally this will not be necessary.

In the simplest case, the coating material consists of the redispersion containing, for example, from 10 to 40 weight percent, and preferably from 20 to 35 weight percent, of the emulsion polymer. As a rule, the coating material will further contain auxiliary agents such as pigments, talc, flow control agents, wetting agents, gloss imparting additives, plasticizers, etc., which usually are separately dispersed in water and added later. However, these auxiliaries may also be incorporated directly into the redispersion. The amount of binder ranges from 10 to 100 weight percent, and preferably from 30 to 90 weight percent, based on the total solids. Solids content and viscosity of the coating material will depend on the method of application. Generally the viscosity will range from 5 to 40 mPa/sec.

Any of the usual coating methods may be used, including the kettle coating commonly employed with dragées, or the fluidized bed coating used with pharmaceutical dosage forms generally.

The coating material is usually applied in an amount from 0.5 to 10 mg of solids per square centimeter of dosage form to give a coating thickness ranging from 1 to 100 microns. As with other coating processes, the coating material may be applied in portions in several layers, drying being effected between them. Moreover, the coating material may be applied continuously and at the same time dried with slightly heated air. Generally it will suffice to heat the surface of the dosage forms to be coated to less than 40° C., usually even to less than 35° C., and preferably to between 25° C. and 35° C., air inlet temperatures ranging from 40° C. to 70° C. being required depending on the rate of evaporation and on the design of the apparatus.

A better understanding of the present invention and of its many advantages will be had by referring to the following Examples, given by way of illustration.

EXAMPLE 1

A dispersion having a solids content of 30 percent was prepared by the emulsion polymerization of equal parts by weight of methacrylic acid and ethyl acrylate, the average diameter of the latex particles being 100 nanometers (nm). This dispersion was freeze dried and the dry residue was crushed to a coarse powder. 3.6 g NaOH were then dissolved in 1 liter of water and 300 g of the above powder were stirred in. This amount of NaOH was sufficient for the conversion to the Na-salt form of 2.6 percent by weight of the original polymer. After further stirring, a milky dispersion was obtained within 5 minutes which contained no particles of a size over 10 microns, as determined by "Grindometer" measurement. Particle size determination with a "Nanosizer" showed that the average diameter of the latex particles was 120 nm. 1,000 g of the dispersion so obtained were sprayed onto 3 kg of tablets. The coating so produced was a smooth, uniform film which proved resistant to artificial gastric juice in conformity with the German Pharmacopoeia. The tablets disintegrated in artificial intestinal juice of pH 7.5 within 15 minutes.

EXAMPLE 2

A fine powder was obtained from a 40% aqueous dispersion of a resin comprising 30% of methacrylic acid and 70% of methyl methacrylate by spray drying at 60° C. 300 g of that powder were then stirred into 1 liter water together with 54 ml of N NaOH. This amount of NaOH was sufficient for the conversion to the Na-salt form of 1.55 percent by weight of the original polymer. Five minutes later a latexlike dispersion had formed. A "Grindometer" test showed that none of the particles exceeded 10 microns in size. Less than 20 percent of the particles were found in the range from 5 to 10 microns. The dispersion was used as in Example 1 to coat tablets, a smooth coating resistant to artificial gastric juice being obtained. The tablets disintegrated within 15 minutes in artificial intestinal juice at pH 7.5.

EXAMPLE 3

100 g of a freeze-dried emulsion polymer of equal parts by weight of methacrylic acid and of ethyl acrylate were added to 220 g water and 3 g of an aqueous 1N ammonia solution were then added dropwise with stirring. This amount of $NH_3$ was sufficient for the conversion to the ammonium salt form of 0.26 percent by weight of the original polymer. After 15 minutes' stirring, a latexlike dispersion had formed. More than 99.5 percent of the material was redispersed and passed through a screen with a clear mesh opening of 0.1 mm. The "Grindometer" test showed that there were no particles over 5 microns. The Brookfield viscosity was 12.5 mPa/sec. The dispersion was used as in Example 1 to coat tablets, a coating being obtained which had the same properties as that obtained in Example 1.

EXAMPLE 4

300 g of a freeze-dried emulsion polymer prepared from 50 percent by weight of dimethylaminoneopentyl methacrylate, 30 percent by weight of ethylacrylate, and 20 percent by weight of methylmethacrylate were added to 300 g of water and pumped continuously through a homogenizer (Fryma-mill). During this process, 42 g of a 1 molar aqueous solution of hydrochloric acid were added within 10 min to convert 2.8 percent by weight of the polymer to the hydrochloride salt form. By further continuous pumping for 20 minutes, a milky, fine dispersion was formed which was used for the coating process as described in Example 1 to give a coating soluble in artificial gastric juice.

EXAMPLE 5

A dispersion having a solids content of 30 percent was prepared by emulsion polymerization of 150 g of methacrylic acid and 150 g of ethylacrylate emulsified in 700 g of water. After the end of polymerization, a solution of 3.6 g NaOH in 100 g water was added, which amount was sufficient for the conversion to the corresponding salt form of 2.6 percent by weight of the polymers. The mixture was stirred for 30 min and freeze-dried. The remaining cake was powdered and dispersed in a solution of 30 g Tween 80 in 1 kg of water by intensive mixing with a high speed stirrer. 75 g of polyethylene glycol 6000 in 150 g of water and 100 g of talc were added to the resulting dispersion and the resulting coating mixture was sprayed on 10 kg of tablets as an isolating layer.

EXAMPLE 6

250 g of a freeze-dried powder prepared by emulsion polymerization of 125 g of methacrylic acid and 125 g of ethylacrylate were mixed with 4.8 g of tris (hydroxymethyl)-aminomethane (dry substance), which amount was sufficient for the conversion to the corresponding salt form of 1.4 percent by weight of the polymer. The mixture was added in portions of approximately 20 g to 750 g of water while mixing with a high speed stirrer. After addition of all the powder the mixture was stirred for additional 15 minutes and used as a coating dispersion.

EXAMPLE 7

The procedure of Example 1 was repeated with the exception that a dispersion was prepared from 50 percent by weight of methacrylic acid, 45 percent by weight of ethyl acrylate, and 5 percent by weight of N-vinyl pyrrolidone. The coating so produced had similar properties to those of the coating of Example 1.

EXAMPLE 8

The procedure of Example 2 was repeated with the exception that a dispersion prepared from 30 percent by weight of methacrylic acid, 60 percent by weight of methyl methacrylate, and 10 percent by weight of styrene was used. The coating so produced had similar properties to those of the coating prepared according to Example 2.

What is claimed is:

1. A method for making an aqueous dispersion of a synthetic resin binder, said dispersion being adaptable to the coating of pharmaceutical dosage forms, which method comprises adding a powdered synthetic resin binder, capable of salt formation, to water and dispersing said resin in the presence of such an amount of a salt forming agent reacting with said resin that, after reaction from 0.1 to 10 percent of said resin, by weight, is present in salt form, said resin being prepared by the free radical emulsion polymerization of
   (A) from 20 to 85 percent by weight of at least one alkyl acrylate or alkyl methacrylate,
   (B) from 80 to 15 percent by weight of at least one vinyl or vinylidene monomer having an amino or carboxylic acid group capable of salt formation,
   (C) from 0 to 30 percent by weight of at least one other vinyl or vinylidene monomer copolymerizable with (A) and (B).

2. A method as in claim 1 wherein from 0.5 to 5 percent of said resin, by weight, is present in salt from after dispersion.

3. A method as in claim 1 wherein said powdered resin comprises loosely aggregated fine particles and, after dispersion, at least 80 percent of the resin is present as particles having a diameter from 0.1 to 5 microns.

4. A method as in claim 1 wherein from 0 to 10 percent by weight of monomer (B) is present in said resin in salt form prior to dispersion.

5. A method as in claim 1 wherein said salt forming agent is present admixed with said powdered resin.

6. A method as in claim 1 wherein said salt forming agent is present in said water when said powdered resin is added.

7. A method as in claim 1 wherein said powdered resin is first added to said water and then said salt forming agent is added to disperse said resin.

8. A powdered mixture suitable for dispersion in water to form an aqueous dispersion adaptable to the coating of pharmaceutical dosage forms, said mixture comprising a powdered synthetic resin prepared by the free radical emulsion polymerization of
   (A) from 20 to 85 percent by weight of at least one alkyl acrylate or alkyl methacrylate,
   (B) from 80 to 15 percent by weight of at least one vinyl or vinylidene monomer having an amino or carboxylic acid group capable of salt formation,
   (C) from 0 to 30 percent by weight of at least one other vinyl or vinylidene monomer copolymerizable with (A) and (B),
and such an amount of a powered agent capable of forming a salt with said resin as will salify from 0.1 to 10 percent of said resin, by weight, on reaction therewith.

9. A powdered mixture as in claim 8 wherein said powdered agent is present in said mixture in an amount as will salify from 0.5 to 5 percent of said resin, by weight, on reaction therewith.

* * * * *